United States Patent [19]
Scrivner et al.

[11] Patent Number: 5,973,595
[45] Date of Patent: Oct. 26, 1999

[54] BODY CAVITY METAL DETECTION SYSTEM

[75] Inventors: Thomas V. Scrivner; Robert F. Turner, both of El Paso, Tex.

[73] Assignee: Ranger Security Detectors, Inc., El Paso, Tex.

[21] Appl. No.: 08/977,611

[22] Filed: Nov. 25, 1997

[51] Int. Cl.$^6$ .................................................. G08B 13/24
[52] U.S. Cl. .................. 340/551; 340/572.6; 340/573.1; 324/243; 600/550
[58] Field of Search .................................. 340/551, 573, 340/574, 605, 572, 572.1, 572.4, 572.6, 573.1, 573.3, 573.4; 324/243, 236, 329; 600/550

[56] References Cited

U.S. PATENT DOCUMENTS

| | | | |
|---|---|---|---|
| 4,431,005 | 2/1984 | McCormick | 340/551 |
| 4,526,177 | 7/1985 | Rudy et al. | 600/550 |
| 4,677,384 | 6/1987 | Payne | 324/329 |
| 4,906,973 | 3/1990 | Karbowski et al. | 340/551 |
| 5,521,583 | 5/1996 | Frahm et al. | 340/551 |
| 5,649,546 | 7/1997 | Steinbeck | 340/551 |
| 5,672,807 | 9/1997 | Gonsalves | 340/515 |
| 5,680,103 | 10/1997 | Turner et al. | 340/551 |
| 5,747,719 | 5/1998 | Bottesch | 340/573 |

FOREIGN PATENT DOCUMENTS

| | | | |
|---|---|---|---|
| 2161138 | 6/1973 | Germany | G01V 3/12 |
| 4410402 | 9/1994 | Germany | B60R 21/32 |
| 2284990 | 6/1995 | United Kingdom . | |
| WO 9729683 | 8/1997 | WIPO | A61B 5/05 |

*Primary Examiner*—Jeffery A. Hofsass
*Assistant Examiner*—Van T. Trieu
*Attorney, Agent, or Firm*—Baker & Botts, L.L.P.

[57] ABSTRACT

A metal detection system for detecting metal within a body cavity of an individual. The metal detection system includes a first metal detector for detecting metal within an anal/vagina body cavity of an individual, and a second metal detector for detecting metal within an oral/facial body cavity of the individual. A chair supports a first detector sensor and a second detector sensor that connects to the first metal detector and the second metal detector, respectively. The system further includes a processor that interconnects with the first and second detectors. The processor connects to a control panel having indicators responsive to a first output signal and second output signal generated upon detection of metal by the first metal detector and the second metal detector, respectively.

11 Claims, 2 Drawing Sheets

BODY CAVITY METAL DETECTION SYSTEM

TECHNICAL FIELD

The present invention relates to a body cavity metal detection system and, more particularly, to a metal detection system for non-invasive detecting of metal within a body cavity of an individual.

BACKGROUND OF THE INVENTION

Metal detectors have become a commonly utilized piece of security equipment in locations such as prisons and manufacturing facilities. A primary function of metal detectors is to accurately detect the presence of hidden illicit metal objects located on an individual. Until recently, metal detectors for detecting metal within a body cavity of the individual had limited use.

Traditional methods of searching a body cavity of an individual were both uncomfortable and a timely excursion for all parties concerned. Often, a body cavity search would be neglected because of the attendant difficulties thereby allowing transportation of illicit metal objects into a prison or theft of precious metals from manufacturing facilities.

Presently, metal detectors are available and may be utilized to detect metal within a body cavity of an individual. However, there is no known body cavity metal detection system designed to interact effectively and safely with an individual during a body cavity search for illicit metal objects.

Accordingly, there is a need for a metal detection system that effectively and safely detects metal within the body cavity of an individual. There is also a requirement to provide a metal detector system that has been ergonomically designed. These and other needs are satisfied by the body cavity metal detection system of the present invention.

SUMMARY OF THE INVENTION

The present invention is a metal detection system for non-invasive detecting of metal within a body cavity of an individual. The metal detection system includes a first metal detector for detecting metal within an anal/vagina body cavity of an individual, and a second metal detector for detecting metal within an oral/facial body cavity of the individual. A support structure, for example a chair, supports a first detector sensor and a second detector sensor that correspond with the first metal detector and the second metal detector. Also, the system further includes an enclosure that interconnects with the first and second detector sensors and surrounds the first and second metal detectors. The enclosure has a control panel with indicators that are responsive to a first output signal and second output signal generated upon detection of metal by the first metal detector and the second metal detector, respectively.

BRIEF DESCRIPTION OF THE DRAWINGS

A more complete understanding of the invention may be had by reference to the following Detailed Description when taken in conjunction with the accompanying Drawings wherein.

DETAILED DESCRIPTION OF THE DRAWINGS

Figure 1:
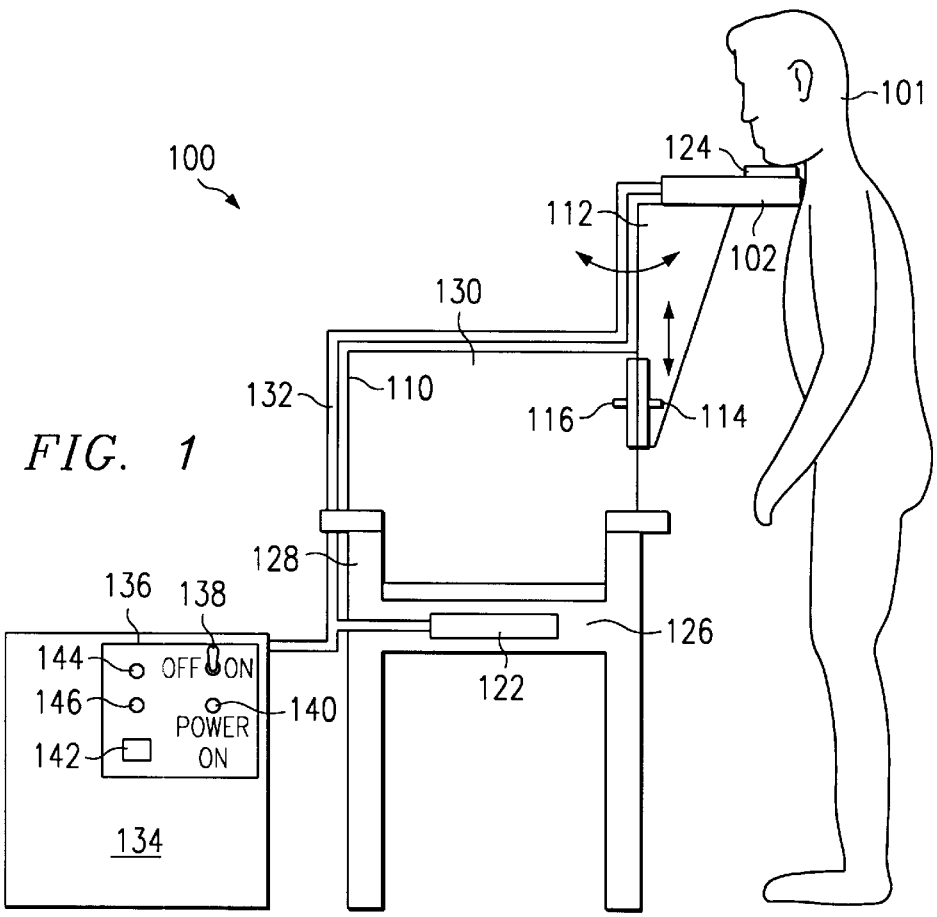
FIG. 1 is a side view of a metal detection system supported on a chair for detecting metal within a body cavity of an individual.

Referring to the Drawings, wherein like numerals represent like parts throughout the several views, there is disclosed a metal detection system 100 in accordance with the present invention.

A metal detector that detects metal objects such as illustrated and described in U.S. Pat. No. 5,521,583 may be used to detect metal objects. The metal detector as disclosed in U.S. Pat. No. 5,521,583 is incorporated into this specification.

Referring to FIG. 1, there is shown the metal detection system 100 including a chair 110. The chair 110 includes a support platform 112 extending therefrom. The support platform 112 includes a vertical adjuster 114 and a rotational adjuster 116. The vertical adjuster 114 permits an upward or downward movement of the support platform 112 in relation to the chair 110. A desirable height of the support platform 112 depends on the height of an individual 101. The rotational adjuster 116 rotates the support platform 112 inward or outward from the chair 110.

A second detector sensor 102 may be rigidly fixed or rotatably connected to the support platform 112. The second detector sensor is used to detect metal object(s) located in the oral/facial region of the individual 101. The second detector sensor 102 may further include a chin rest 124 to properly locate a head of the individual 101 in order to maximize the detection capabilities of the metal detection system 100.

A first detector sensor 122 is mounted to a lower portion of the chair 110 to detect metal objects located in the anal/vagina region (the "a/v region") of the individual 101. Preferably, the first detector sensor 122 is located on or within a seat 126 of the chair 110. However, the first detector sensor 122 may be located on or within a side 128 or a back 130 of the chair 110 and still function properly.

The second detector sensor 120 and the first detector sensor 122 are electrically connected via cables located in a raceway 132 to a control box 134. The control box 134 houses the electronic components associated with the metal detection system 100 and includes a control panel 136. A detailed description of the first detector sensor 122 and the second detector sensor 120 will be discussed later.

Figure 2:
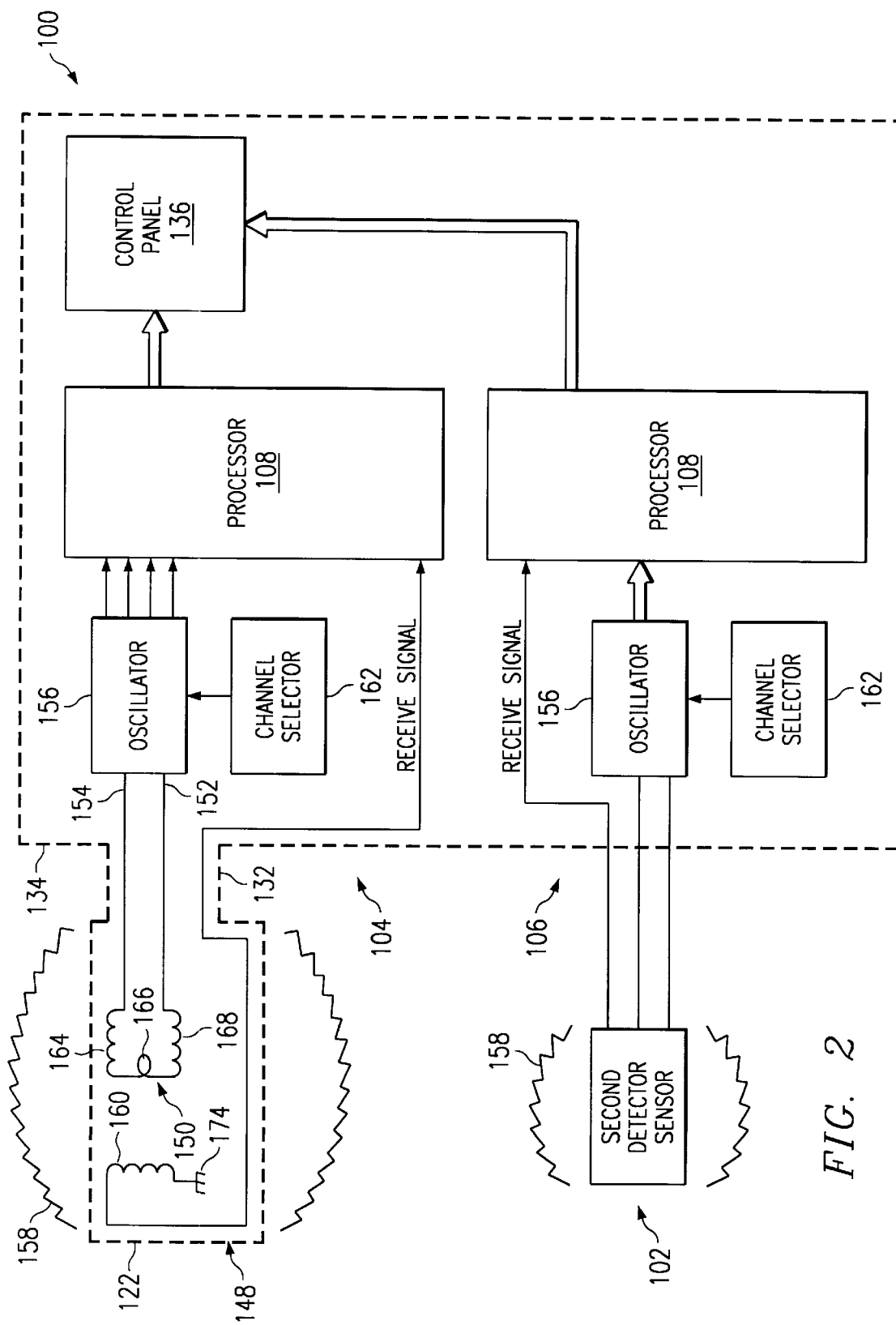
FIG. 2 is a block diagram of the metal detection system of the present invention.

Referring to FIG. 2, the metal detection system 100 includes a first metal detector 104 and a second metal detector 106. The first metal detector 104 is electrically connected to the first detector sensor 122, and the second metal detector 106 is electrically connected to the second detector sensor 102. Reference is made to U.S. Pat. No. 5,521,583 for a detailed description of the first metal detector 104 and the second metal detector 106. Each metal detector 104 and 106 includes a processor 108 that is detailed in U.S. Pat. No. 5,521,583. Although in the preferred embodiment of the processor 108 analog circuits are described, it will, of course, be understood that the requisite detection and processing functions may be implemented using digital signal processing techniques.

The control panel 136 includes control knobs and alarm indicators. The control knobs include a power switch 138 and power-on light 140. The power switch 138 is used to turn on or off the metal detection system 100. The power-on light 140 is illuminated whenever the metal detection system 100 is operational. The metal detection system 100 is typically connected to a conventional 120 VAC power source that is transformed into whatever voltage is required by the various electronic components.

The alarm indicators typically include an audible alarm 142, a head indicator 144 and an a/v region indicator 146. The audible alarm 142 is actuated upon detection of a metal object by either the first metal detector 104 or the second metal detector 106. The head indicator 144 is actuated upon detection of metal objects within the oral/facial region of the individual 101. Likewise, the a/v region indicator 146 is actuated upon detection of metal objects within the anal/vagina region of the individual 101.

The metal detection system 100 will be described in terms of the metal detector 104, however, there will commonly be two such metal detectors incorporated in a detection system. The metal detection system 100 utilizes a multiple turn frequency coil set 148 as a part of the first detector sensor 122. The coil set 148 is positioned in proximity to the body cavity of the individual 101 for scanning and detection of metal objects. The coil set 148 includes a field generation coil 150 having one end coupled to an alternating current port 152 and another end coupled to another alternating current port 154 of an oscillator 156. The field generation coil 150 is excited in phase by the oscillator 156 to generate a single alternating current electromagnetic field 158 concentrated with substantially uniform field density around and through the individual 101.

The presence of metal objects within a body cavity of the individual 101 causes a disturbance in the electromagnetic field 158 generated by the field generation coils 150. This disturbance is sensed by a receive coil 160 that is a part of the coil set 148. The receive coil 160 has one end connected to the processor 108. Reference is made to U.S. Pat. No. 5,521,583 for a detailed description of the processor 108 that generates an output signal indicative of the presence of the metal object within the body cavity.

The oscillator 156 is connected to a channel selector circuit 162 that enables an operator of the metal detection system 100 to select different frequencies (preferably centering around 6 kilohertz, with 100 hertz separating the channels available for selection) for the generated alternating current electromagnetic field 158. Slight phase adjustments in the generated alternating current signal are also possible with the selector circuit 162. With proper frequency and phase selection, multiple metal detectors may be operated in close proximity to each other with minimal interference to adversely affect performance.

An output of the processor 108 is connected to the control panel 136 having the alarm indicators and the control knobs 17 as discussed earlier.

The metal detector 106 includes components similar to those described with reference to the metal detector 106. The metal detector 106 connects to the second detector sensor 102.

Figure 3:
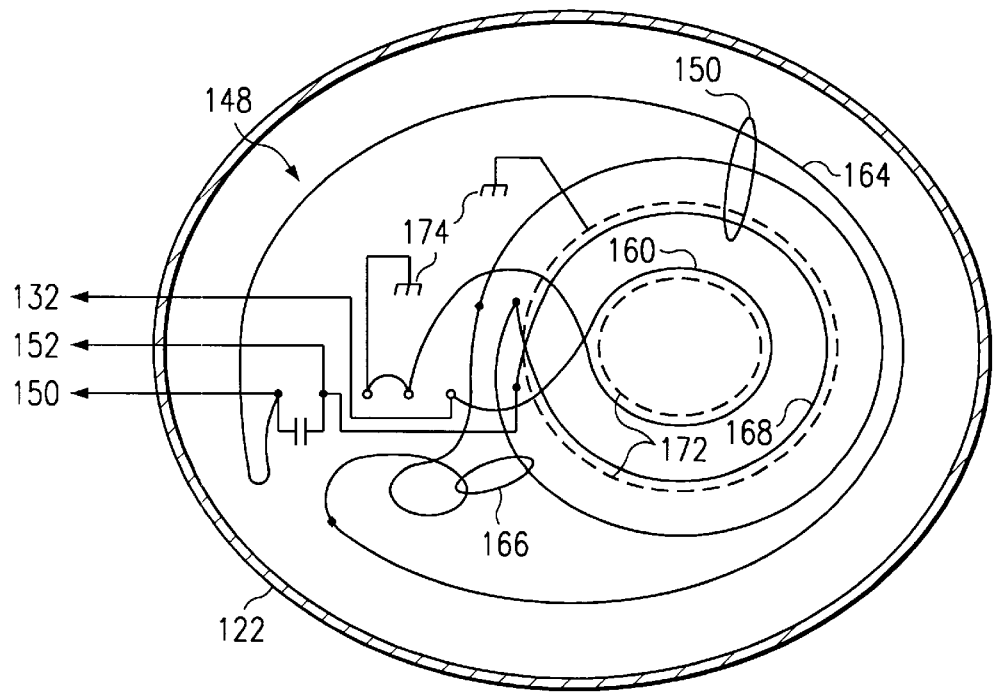
FIG. 3 illustrates the geometry of a coil set disposed within a detector sensor.

Referring now to FIG. 3, there is shown the geometry of the coil set 148 disposed within the detector sensor 122. Although illustrated in FIG. 2 as a single coil, the field generation coil 150 is preferably comprised of three separate elements. The first element is a transmit coil 164, the second element is a null adjust loop 166, and the third element is a feedback coil 168. The three elements of the field generation coil 150 are connected in series.

The transmit coil 164 is shielded with a resistive shield (not shown) connected to system ground 174. The receive coil 160 and feedback coil 168 are also shielded with a resistive shield 172 connected to system ground 174. Termination of the resistive shields to the system ground 174 provides suppression of primary electromechanical interference and radio frequency interference. Moreover, the field generation coil 150 and the receive coil 160 are co-planar and coaxially aligned with each other.

While the present invention has been described with reference to the illustrated embodiment, it is not intended to limit the invention, but on the contrary, it is intended to cover such alternatives, modifications, and equivalents as may be included in the spirit and scope of the invention as defined in the following claims.

We claim:

1. A metal detection system for detecting metal within the body cavities of an individual comprising:

a first metal detector having a first non-invasive detector sensor, said first non-invasive detector sensor positioned in proximity to the anal/vaginal area of an individual for detecting metal within an anal/vagina body cavity of an individual and generating a first output signal;

a second metal detector having a second non-invasive detector sensor, said second non-invasive detector sensor positioned in proximity to the oral/facial area of an individual for detecting metal within an oral/facial body cavity of the individual and generating a second output signal;

means for supporting an individual to locate the anal/vagina body cavity in proximity to the first detector sensor for detecting metal within the anal/vagina body cavity and to locate the oral/facial body cavity in proximity to the second detector sensor for detecting metal within the oral/facial body cavity; and a processor interconnected to the first and second detectors, said processor responsive to the first output signal and second output signal for activating an indicator identifying the detection of a metal object and the location thereof.

2. The metal detection system in accordance with claim 1 wherein the means for supporting further includes a chair having a support platform extending therefrom, said support platform supporting the second detector sensor.

3. The metal detection system in accordance with claim 2 wherein the chair further includes a seat supporting the first detector sensor.

4. The metal detection system in accordance with claim 1 wherein the means for supporting further includes a vertical adjuster and a rotational adjuster, each adjuster positions the second detector sensor to a desired position.

5. The metal detection system in accordance with claim 1 wherein each metal detector further includes:

an oscillator; and the first and second detector sensors include:

a field generation coil connected to and excited by the oscillator to generate an electromagnetic field disrupted by the presence of metal objects within the body cavity of the individual;

a receive coil responsive to the generated electromagnetic field; and said processor receiving and processing a receive signal from the receive coil of a detector sensor to generate the identification of a metal object.

6. The metal detection system in accordance with claim 5 wherein the field generation coil and the receive coil are substantially co-planar and coaxially aligned with each other within a grounded resistive shield.

7. The metal detection system in accordance with claim 1 further comprising a control panel connected to the processor, said control panel includes first and second alarms corresponding to the first and second metal detectors, said first and second alarms indicate the detection and location of a metal object.

8. The metal detection system in accordance with claim 7 wherein the control panel further includes an alarm for generating an audible alarm upon the detection of a metal object.

9. A metal detection system for detecting metal within a body cavity of an individual comprising:

a chair having a sitting area and a backrest area;

a first non-evasive metal detector mounted to the sitting area of said chair for detecting metal within an anal/vagina region of the individual and a second non-evasive metal detector mounted to the backrest area of said chair for detecting metal within an oral/facial region of the individual, each metal detector including:

a coil set generating an electromagnetic field and responding to an interruption of the electromagnetic field;

a processor for receiving and processing a signal representing an interruption of the electromagnetic field of the coil set to generate an output signal indicative of the presence of the metal object within the anal/vagina region and/or the oral/facial region body cavity disrupting the electromagnetic field; and an alarm responsive to the output signal.

10. A metal detection system for detecting metal within a body cavity of an individual comprising:

at least one non-evasive metal detector having a corresponding non-evasive detector sensor responsive to a metal object within the anal/vagina or the oral/facial region of an individual, said at least one non-evasive metal detector detecting metal within the anal/vagina or oral/facial region of an individual and generating a detection signal;

means for supporting an individual to locate the anal/vagina or oral/facial region in proximity to a corresponding detector sensor; and a processor connected to at least one non-evasive metal detector and responsive to the detection signal for generating an alarm indicating the presence and location of a detected metal object.

11. The metal detection system in accordance with claim 10 wherein the at least one metal detector further includes:

an oscillator;

a field generation coil as a part of the detector sensor, said field generation coil connected to and excited by the oscillator to generate an electromagnetic field disrupted by the presence of metal objects within the body cavity of the individual;

a receive coil as a part of the detector sensor, said receive coil responsive to a disruption of the generated electromagnetic field and outputting a receive signal; and a processor for receiving and processing the receive signal from the receive coil to generate an output signal upon detection of the metal object within a body cavity of an individual.

* * * * *